United States Patent
Ono et al.

(10) Patent No.: US 6,818,800 B2
(45) Date of Patent: Nov. 16, 2004

(54) METHODS FOR PROVIDING LOW-MOLECULAR RADICALS, RADICAL-CARRYING MOLECULES, A POLYMERIZATION CATALYST CONTAINING THEM AND PROCESSES FOR POLYMERIZATION AND POLYMERS PRODUCED THEREBY

(75) Inventors: Taizo Ono, Nagoya (JP); Eiji Hayashi, Nagoya (JP); Haruhiko Fukaya, Nagoya (JP); Tetsuo Shimizu, Settsu (JP)

(73) Assignees: National Institute of Advanced Industrial Science and Technology, Tokyo (JP); Daikin Industries, Ltd., Osaka (JP)

( * ) Notice: Subject to any disclaimer, the term of this patent is extended or adjusted under 35 U.S.C. 154(b) by 72 days.

(21) Appl. No.: 10/291,650

(22) Filed: Nov. 12, 2002

(65) Prior Publication Data

US 2003/0114613 A1 Jun. 19, 2003

(30) Foreign Application Priority Data

Nov. 16, 2001 (JP) ........................... 2001-352475

(51) Int. Cl.[7] .................................... C07C 21/18
(52) U.S. Cl. ................. 570/136; 526/217; 526/222; 570/162
(58) Field of Search .................. 526/217, 222; 570/136, 162

(56) References Cited

U.S. PATENT DOCUMENTS 4,626,608 A   12/1986   Scherer, Jr. et al.

OTHER PUBLICATIONS

Sterlin et al. Journal of Fluorine Chemistry 80 (1996), 77–80.*
Allayarov et al. Journal of Fluorine Chemistry 96 (1999), 57–60.*
Lyakhovetsky et al. Fullerene Science and Technology, 7(2), 263–287 (1999).*

* cited by examiner

Primary Examiner—Helen L. Pezzuto
(74) Attorney, Agent, or Firm—Sughrue Mion, PLLC

(57) ABSTRACT

The present invention is to provide a method for providing a low-molecular radical which comprises releasing a radical having a lower molecular weight from a super-stable perfluoroalkyl-based radical followed by generating the above super-stable perfluoroalkyl-based radical.

The invention is a method for providing a low-molecular radical which comprises a super-stable radical generating reaction for generating a super-stable perfluoroalkyl-based radical from a radical-carrying molecule and a radical releasing reaction for releasing the low-molecular radical from said super-stable perfluoroalkyl-based radical, said radical-carrying molecule being generated as a result of said radical releasing reaction.

25 Claims, No Drawings

METHODS FOR PROVIDING LOW-MOLECULAR RADICALS, RADICAL-CARRYING MOLECULES, A POLYMERIZATION CATALYST CONTAINING THEM AND PROCESSES FOR POLYMERIZATION AND POLYMERS PRODUCED THEREBY

TECHNICAL FIELD

The present invention relates to a method for providing a low-molecular radical, more particularly, a method for generating a low-molecular radical and a radical-carrying molecule from a super-stable perfluoroalkyl-based radical generated from the above radical-carrying molecule.

PRIOR ART

A radical is generated from a radical initiator by heating or irradiating the same in the polymer synthesis, for example, and is utilized. A conventional radical initiator cannot be used as a radical initiator again once it is decomposed to generate a radical.

Among radical initiators, U.S. Pat. No. 2,559,630 discloses bis(perfluoroacyl) peroxide as a fluorine-based radical initiator generating a perfluoroalkyl radical, and N-trifluoromethyl-N-nitrosotrifluoromethanesulfonamide and the like are known (T. Uemoto and A. Ando, Bull. Chem. Soc. Jpn., 59, 447–452(1986)).

As the fluorine-based radical initiator, Japanese Kokoku Publication Hei-1-29175 suggests the utilization of perfluoro(2,4-dimethyl-3-isopropyl-2-pentene), which has an extremely high chemical stability, with an ethylenically unsaturated monomer such as tetrafluoroethylene or chlorfluoroethylene in an aqueous or non-aqueous system.

Such an extremely high stability of perfluoro(2,4-dimethyl-3-isopropyl-2-pentene) is also disclosed in U.S. Pat. No. 4,626,608 and K. V. Scherer, T. Ono, K. Yamanouchi, R. Fernandez, P. Henderson, J. Am. Chem. Soc., 107, 718–719 (1985).

However, the method for re-generating the super-stable perfluoroalkyl-based radical and releasing the reactive radical after releasing a reactive radical having a lower molecular weight from such a super-stable perfluoroalkyl-based radical having an extremely high chemical stability has not been disclosed.

Since such a perfluoroalkyl radical generating reagent is expensive, the development of a radical providing method which allows the same to be utilized repetitively as a radical generator even after generating a radical has been desired. Especially in these years, environmental consciousness emphasizes "atom economy" and "green chemistry" and leads to an increased demand of the development of the radical providing method as described above.

SUMMARY OF THE INVENTION

In view of the above-mentioned state of the art, it is an objective of the present invention to provide a method for providing a low-molecular radical which comprises releasing a radical having a lower molecular weight from a super-stable perfluoroalkyl-based radical followed by generating the above super-stable perfluoroalkyl-based radical.

The invention is a method for providing a low-molecular radical which comprises a super-stable radical generating reaction for generating a super-stable perfluoroalkyl-based radical from a radical-carrying molecule and a radical releasing reaction for releasing the low-molecular radical from said super-stable perfluoroalkyl-based radical, said radical-carrying molecule being generated as a result of said-radical releasing reaction.

The invention is a radical-carrying molecule which is used in the above method for providing the low-molecular radical.

The invention is a process for polymerization which comprises using the low-molecular radical released by the method for providing the above low-molecular radical as a polymerization initiator.

DETAILED DESCRIPTION OF THE INVENTION

In the following, the invention is described in detail.

The method for providing the low-molecular radical according to the invention comprises a super-stable radical generating reaction for generating a super-stable perfluoroalkyl-based radical from a radical-carrying molecule and a radical releasing reaction for releasing the low-molecular radical from said super-stable perfluoroalkyl-based radical, in which said radical-carrying molecule is generated as a result of the above radical releasing reaction.

The above super-stable perfluoroalkyl-based radical is a free radical capable of releasing a low-molecular radical, by heating and the like, whose molecular weight is lower than that of the above super-stable perfluoroalkyl-based radical.

The above super-stable perfluoroalkyl-based radical is a free radical represented by the following general formula (4):

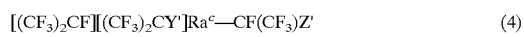

$$[(CF_3)_2CF][(CF_3)_2CY']Ra^c—CF(CF_3)Z' \quad (4)$$

in the formula, $Ra^c$ represents a carbon atom having one unpaired electron, and Y' and Z' are the same or different and each represents F or a low-molecular-pre-radical group, provided that Y' and Z' are not simultaneously F.

The above low-molecular-pre-radical group is a group having the same structure as the above low-molecular radical.

In this specification, the above "low-molecular-pre-radical group" means a group to be released as the above low-molecular radical out of the molecule of the above super-stable perfluoroalkyl-based radical as a result of the radical releasing reaction described below.

Accordingly, the above low-molecular-pre-radical group is a group having the same structure as the above low-molecular radical. In this specification, the above expression "having the same structure" means that the alignment of the constituent atoms is the same.

The above low-molecular-pre-radical group is a straight or branched perfluoroalkyl group having 1 to 16 carbon atoms or a group represented by the following general formula (6):

$$RfQ- \quad (6)$$

in the formula, Q represents a nitrogen atom, an oxygen atom or a sulfur atom, and Rf represents a straight or branched perfluoroalkyl group having 1 to 16 carbon atoms, a linear substituted aminyl group represented by the following general formula (7):

$$Rf_2N— \quad (7)$$

in the formula, each Rf is the same or different from each other and represents a straight or branched perfluoroalkyl group having 1 to 16 carbon atoms, or a cyclic substituted aminyl group represented by the following general formula (8):

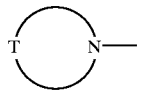
(8)

in the formula, T represents a perfluoroalkylene group having 4 to 6 carbon atoms and having or not having 1 to 2 ethereal oxygen.

The above low-molecular-pre-radical group is preferably a straight or branched perfluoroalkyl group having 1 to 16 carbon atoms, more preferably a trifluoromethyl group.

The above super-stable perfluoroalkyl-based radical is preferably a super-stable perfluoroalkyl radical represented by the following general formula (11):

$$[(CF_3)_2CF][(CF_3)_2CY]Ra^c-CF(CF_3)Z \qquad (11)$$

in the formula, $Ra^c$ represents a carbon atom having one unpaired electron, Y and Z are the same or different and each represents F or Rf, provided that Y and Z are not simultaneously F, and Rf represents a straight or branched perfluoroalkyl group having 1 to 16 carbon atoms, or a super-stable perfluoroalkyl-based radical (AR') represented by the following general formula (5):

$$[(CF_3)_2CF]_2Ra^c-CF(CF_3)Z' \qquad (5)$$

in the formula, $Ra^c$ represents a carbon atom having one unpaired electron, and Z' represents a low-molecular-pre-radical group.

More preferably, the above super-stable perfluoroalkyl-based radical is one represented by the following general formula:

$$[(CF_3)_2CF]_2Ra^c-CF\ (CF_3)Z$$

in the formula, $Ra^c$ represents a carbon atom having one unpaired electron, and Z represents Rf. The above Rf is similar to one defined in the above general formula (11).

In the above general formula (11), while Rf as Y and/or Z is not particularly limited provided that it is a perfluoroalkyl group having 1 to 16 carbon atoms and may be straight or branched, it is preferably a perfluoroalkyl group having 1 to 3 carbon atoms since it is easily purified and analyzed, with a trifluoromethyl group being more preferred. The above Rf is derived from Rf as Y and/or Z in the highly branched perfluoroolefin employed in the super-stable radical generating reaction described below.

In the above general formula (11), $Ra^c$ is a carbon atom having one unpaired electron. The term "carbon atom having one unpaired electron" employed herein means a carbon having, on the atom, an unpaired electron possessed by a free radical.

The super-stable perfluoroalkyl radical represented by the above general formula (11) is a super-stable perfluoroalkyl radical (AR) represented by the following general formula (11a):

$$[(CF_3)_2CF]_2Ra^c-CF(CF_3)Rf \qquad (11a)$$

in the formula, $Ra^c$ represents a carbon atom having one unpaired electron and Rf represents a straight or branched perfluoroalkyl group having 1 to 16 carbon atoms, a super-stable perfluoroalkyl radical (BR) represented by the following general formula (11b):

$$[(CF_3)_2CF][(CF_3)_2CRf]Ra^c-CF(CF_3)Rf \qquad (11b)$$

in the formula, $Ra^c$ represents a carbon atom having one unpaired electron and each Rf is the same or different from each other and represents a straight or branched perfluoroalkyl group having 1 to 16 carbon atoms, or a super-stable perfluoroalkyl radical (CR) represented by the following general formula (11c):

$$[(CF_3)_2CF][(CF_3)_2CRf]Ra^c-CF_2(CF_3) \qquad (11c)$$

in the formula, $Ra^c$ represents a carbon atom having one unpaired electron and Rf represents a straight or branched perfluoroalkyl group having 1 to 16 carbon atoms.

The above super-stable perfluoroalkyl radical (AR) is preferably perfluoro(2,4-dimethyl-3-isopropyl-3-pentyl) (hereinafter referred to as "super-stable perfluoroalkyl radical (aR)"). The above super-stable perfluoroalkyl radical (BR) is preferably perfluoro(2,4,4-trimethyl-3-isopropyl-3-pentyl) (hereinafter referred to as "super-stable perfluoroalkyl radical (bR)"). The above super-stable perfluoroalkyl radical (CR) is preferably perfluoro(4,4-dimethyl-3-isopropyl-3-pentyl) (hereinafter referred to as "super-stable perfluoroalkyl radical (cR)").

The above super-stable perfluoroalkyl-based radical is preferably the super-stable perfluoroalkyl radical (AR), more preferably the super-stable perfluoroalkyl radical (aR).

The above super-stable perfluoroalkyl radical is sufficiently stable at a temperature usually below 90° C., depending on the chemical structure, however. While the above super-stable perfluoroalkyl radical is decomposed by the radical releasing reaction described below to generate the low-molecular radical, it has a half-life of 6 hours or longer at a temperature usually below 90° C.

Among the above super-stable perfluoroalkyl radicals, especially, the above super-stable perfluoroalkyl radical (aR) is sufficiently stable such that it does not react even with a pure fluorine gas at 0° C., and undergoes no chemical change at room temperature over a period longer than one year. The above super-stable perfluoroalkyl radical (aR) is decomposed at a half-life of about 6 hours when heated at 90° C. to generate a free trifluoromethyl radical.

The above super-stable perfluoroalkyl-based radical may contain a nitrogen atom, oxygen atom and/or sulfur atom within the molecule, unlike to the above super-stable perfluoroalkyl radical.

In this specification, the above "low-molecular radical" means a free radical derived from a portion of the chemical structure of the above super-stable perfluoroalkyl-based radical. Accordingly, the above low-molecular radical has a molecular weight which is lower than that of the super-stable perfluoroalkyl-based radical. The low-molecular radical described above is usually a free radical generated when a low-molecular-pre-radical group possessed by the above super-stable perfluoroalkyl-based radical is cleaved and released out of the molecule. The above low-molecular radical, when the above low-molecular-pre-radical group is for example a trifluoromethyl group, is a free trifluoromethyl radical generated as a result of β-scission of the super-stable perfluoroalkyl radical.

The above low-molecular radical is a straight or branched perfluoroalkyl having 1 to 16 carbon atoms or a free radical represented by the following general formula (1):

$$RfRa^h \qquad (1)$$

in the formula, $Ra^h$ represents a nitrogen atom having two unpaired electrons, an oxygen atom having one unpaired electron or a sulfur atom having one unpaired electron, and Rf represents a straight or branched perfluoroalkyl group having 1 to 16 carbon atoms.

The above low-molecular radical may also be a linear substituted aminyl represented by the following general formula (2):

$$Rf_2 Ra^N \qquad (2)$$

in the formula, $Ra^N$ represents a nitrogen atom having one unpaired electron and each Rf is the same or different from each other and represents a straight or branched perfluoroalkyl group having 1 to 16 carbon atoms,
or a cyclic substituted aminyl represented by the following general formula (3):

(3)

in the formula, $Ra^N$ is defined as described above, T represents a perfluoroalkylene group having 4 to 6 carbon atoms and having or not having 1 to 2 ethereal oxygen.

The above low-molecular radical is preferably a straight or branched perfluoroalkyl having 1 to 16 carbon atoms, more preferably trifluoromethyl.

In this specification, the above "radical releasing reaction" means a reaction by which the above low-molecular radical is released from the above super-stable perfluoroalkyl-based radical and the radical-carrying molecule is regenerated. The release of the above low-molecular radical is usually carried out by heat and/or light.

While the above radical releasing reaction is not particularly limited provided that it releases the above low-molecular radical, it may for example be the reaction in which the super-stable perfluoroalkyl radical (aR) is heated at 90° C. to effect β-scission whereby allowing a trifluoromethyl radical to be generated and perfluoro(4-methyl-3-isopropyl-2-pentene) as a radical-carrying molecule is formed almost quantitatively. The above super-stable perfluoroalkyl radical (aR) is sufficiently stable such that it does not react even with a pure fluorine gas at 0° C., and undergoes absolutely no change over a period of the order of years at room temperature.

In the present invention, the above "radical-carrying molecule" is one generated as a result of the above radical releasing reaction, and means a molecule which can be introduced with the above-described low-molecular-pre-radical group and can release the above low-molecular radical by heat, light and the like, where necessary.

The above radical-carrying molecule is preferably a hexafluoropropene trimer such as perfluoro(2,4-dimethyl-3-ethyl-2-pentene) (hereinafter referred to as "trimer A"), perfluoro(4-methyl-3-isopropyl-2-pentene) (hereinafter referred to as "trimer B") and perfluoro(2,4-dimethyl-3-heptene) (hereinafter referred to as "trimer C"). Among those listed above, the above trimer A and the above trimer B are preferred.

The above trimer B can be obtained easily in a high yield by methods described in references (W. Dmowski, W. T. Flowers and R. N. Haszeldine, J. Fluorine Chem., 9, 94–96 (1977)). Since the resultant trimer B is highly volatile, it is recovered easily into a condenser cooled under reduced pressure in the polymer synthesis. Since the trimer B is easily separated as a fluoro-layer in an organic solvent, it can be recovered very easily.

As the above radical-carrying molecule, the trimer B is more preferred since it is desirable for generating the above super-stable perfluoroalkyl radical (aR) which is a preferred species among the above-mentioned super-stable perfluoroalkyl radicals and can be recovered easily as a radical-carrying molecule because of its easy separation as a fluoro-layer in an organic solvent.

As the above hexafluoropropene trimer, one or two or more species can be used, thus, for example, only the above trimer A, only the above trimer B, a combination of the above trimer A and the above trimer B, or the mixture of these with the above trimer C may be employed. When the above trimer C is mixed, the above trimer C is preferably employed in a small amount for the purpose of raising the purity in the reaction solution.

The above super-stable radical generating reaction comprises introducing the low-molecular-pre-radical group into the radical-carrying molecule. The above low-molecular-pre-radical group is similar to the one described above as one contained within the molecule of the super-stable perfluoroalkyl-based radical. The above super-stable radical generating reaction is a reaction by which the above super-stable perfluoroalkyl-based radical is generated from the above radical-carrying molecule.

In the above super-stable radical generating reaction, the introduction of the low-molecular-pre-radical group into the radical-carrying molecule can be carried out by the following method, for example, when the super-stable perfluoroalkyl radical represented by the above general formula (11) is to be obtained.

Thus, in such case, the above super-stable radical generating reaction comprises using a hexafluoropropene trimer as the above radical-carrying molecule and reacting the above hexafluoropropene trimer with a trialkylperfluoroalkylsilane represented by the following general formula (9):

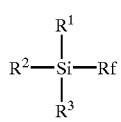

(9)

in the formula, Rf represents a straight or branched perfluoroalkyl group having 1 to 16 carbon atoms, and $R^1$, $R^2$ and $R^3$ are the same or different and each represents an alkyl group having 1 to 3 carbon atoms,
in an aprotic polar solvent using a fluoride ion as a catalyst to thereby form a highly branched perfluoroolefin.

The above highly branched perfluoroolefin is represented by the following general formula (10):

$$[(CF_3)_2CF][(CF_3)_2CY]C=C(CF_3)Z \qquad (10)$$

in the formula, Y and Z are the same or different and each represents F or Rf, provided that Y and Z are not simultaneously F, and Rf is defined as described above.

Accordingly, the above highly branched perfluoroolefin is a highly branched perfluoroolefin (A) represented by the following general formula (12):

$$[(CF_3)_2CF]_2C=C(CF_3)Rf \qquad (12)$$

in the formula, Rf represents a straight or branched perfluoroalkyl group having 1 to 16 carbon atoms,
a highly branched perfluoroolefin (B) represented by the following general formula (13):

$$[(CF_3)_2CF][(CF_3)_2CRf]C=C(CF_3)Rf \qquad (13)$$

in the formula, each Rf is the same or different from each other and represents a straight or branched perfluoroalkyl group having 1 to 16 carbon atoms,
or a highly branched perfluoroolefin (C) represented by the following general formula (15):

  (15)

in the formula, Rf represents a straight or branched perfluoroalkyl group having 1 to 16 carbon atoms.

While the above Rf is not particularly limited provided that it is a perfluoroalkyl group having 1 to 16 carbon atoms and may be straight or branched, it is preferably a perfluoroalkyl group having 1 to 3 carbon atoms since these are easily purified and analyzed, with trifluoromethyl group being more preferred.

In the above general formula (10), Y is preferably Rf. In such case, the above highly branched perfluoroolefin is the above highly branched perfluoroolefin (B) or the above highly branched perfluoroolefin (C). While the above highly branched perfluoroolefin (C) may be any of two kinds of geometric isomers, Z form is more preferred than E form because of a less steric hindrance and a sufficient stability.

The above highly branched perfluoroolefin (A) is preferably perfluoro(2,4-dimethyl-3-isopropyl-2-pentene) (hereinafter referred to as "highly branched perfluoroolefin (a)") The above highly branched perfluoroolefin (B) is preferably perfluoro(2,4,4-trimethyl-3-isopropyl-2-pentene) (hereinafter referred to as "highly branched perfluoroolefin (b)"). The above highly branched perfluoroolefin (C) is preferably perfluoro(4,4-dimethyl-3-isopropyl-2-pentene) (hereinafter referred to as "highly branched perfluoroolefin (c)").

The above highly branched perfluoroolefin is utilized not only as an intermediate for synthesizing surfactants, pharmaceuticals and pesticides, but also as a precursor for the super-stable perfluoroalkyl radical.

While the above trialkylperfluoroalkylsilane is not particularly limited provided that it is represented by the above general formula (9), Rf in the above general formula (9) is preferably a straight or branched perfluoroalkyl group having 1 to 3 carbon atoms, with a trifluoromethyl group being more preferred.

Rf in the above general formula (9) is a low-molecular-pre-radical group to be introduced into the above radical-carrying molecule. Thus, Rf in the above general formula (10) in the resultant highly branched perfluoroolefin is derived from Rf of the above general formula (9) in the above trialkylperfluoroalkylsilane molecule.

$R^1$, $R^2$ or $R^3$ in the above general formula (9) is preferably a methyl group. $R^1$, $R^2$ and $R^3$ are preferably the same to one another, and it is more preferable that all are methyl groups.

The trialkylperfluoroalkylsilane described above is preferably trifluoromethyltrimethylsilane in view of the cost of the raw material.

The aprotic polar solvent employed in the stage of synthesizing the above highly branched perfluoroolefin is not particularly limited, and may for example be a Glyme-based solvent, dimethyl sulfoxide (DMSO), dimethyl acetamide (DMA), dimethyl formamide (DMF), 1-methyl-2-pyrrolidone (NMP), and 1,3-dimethyl-2-imidazolidinone (DMI) and the like. The Glyme-based solvent mentioned above may for example be diethylene glycol dimethyl ether, triethylene glycol dimethyl ether, tetraethylene glycol dimethyl ether, triethylene glycol diethyl ether, tetraethylene glycol diethyl ether and the like, as well as higher homologues thereof.

The above aprotic polar solvent is preferably dimethyl formamide (DMF), 1-methyl-2-pyrrolidone (NMP) and 1,3-dimethyl-2-imidazolidinone (DMI) because of generally higher reaction rates, with 1,3-dimethyl-2-imidazolidinone (DMI) being more preferred because of higher reaction rate and higher selectivity.

The above super-stable radical generation reaction uses the fluoride ion as a catalyst at the stage of synthesizing the highly branched perfluoroolefin. The above fluoride ion is enabled to act as a catalyst by using a compound which generates the fluoride ion.

Such a compound is not particularly limited provided that it can generate a fluoride ion, and may for example be sodium fluoride, potassium fluoride, acidic potassium fluoride, cesium fluoride, tetrabutylammonium fluoride, tetramethylammonium fluoride, tris(dimethylamino)sulfonium trimethylsilyl difluoride, tetrabutylammonium difluorotriphenyl stannate, pyridinium (hydrogen polyfluoride), triethylamine (hydrogen trifluoride) and the like. Among those listed above, pyridinium (hydrogen polyfluoride) is referred to also as Olah reagent.

While the above highly branched perfluoroolefin is not particularly limited provided that it is represented by the above general formula (10), it is preferably the above highly branched perfluoroolefin (A), more preferably the above highly branched perfluoroolefin (a). The above highly branched perfluoroolefin may preferably be the above highly branched perfluoroolefin (b) and the above highly branched perfluoroolefin (c).

The above highly branched perfluoroolefin is generally obtained as a mixture of at least two species selected from the group consisting of the above highly branched perfluoroolefin (A), the above highly branched perfluoroolefin (B) and the above highly branched perfluoroolefin (C), although it may vary depending on the species and the amount of addition of the radical-carrying molecule and the aprotic polar solvent as well as the reaction conditions. The following scheme shows the example in case that Rf is a trifluoromethyl group.

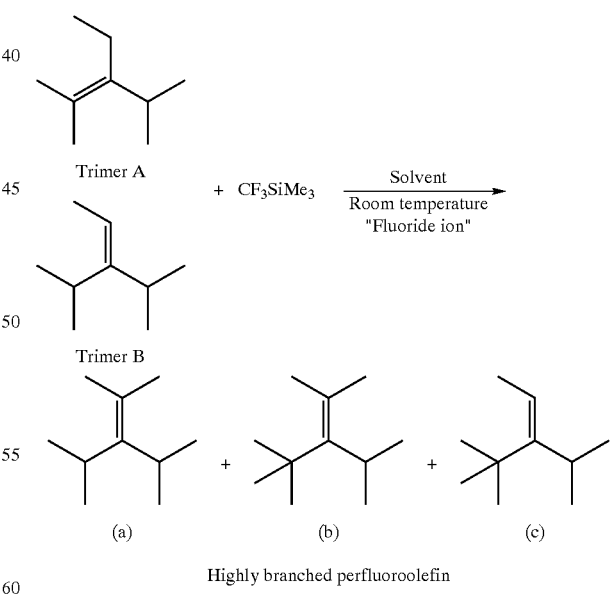

Highly branched perfluoroolefin

As the above highly branched perfluoroolefin, when the trimer A is employed as a radical-carrying molecule, the tendency is such that an yield of the highly branched perfluoroolefin (B) is high, for example 15 to 80% by weight, an yield of the highly branched perfluoroolefin (C) is significantly lower than the yield of the highly branched perfluoroolefin (B), for example 10 to 50% by weight, and an yield of the highly branched perfluoroolefin (A) is 5% by weight or less and may substantially be zero in some cases.

As the above highly branched perfluoroolefin, when the trimer B is employed as a radical-carrying molecule, the tendency is such that an yield of the highly branched perfluoroolefin (A) is high, for example 30 to 95% by weight, an yield of the highly branched perfluoroolefin (B) is significantly lower than the yield of the highly branched perfluoroolefin (A), for example 45% by weight or less, and an yield of the highly branched perfluoroolefin (C) is 5% by weight or less and may substantially be zero in some cases.

For the purpose of obtaining the above highly branched perfluoroolefin (A) selectively, 1,3-dimethyl-2-imidazolidinone is preferably employed as the aprotic polar solvent. By using 1,3-dimethyl-2-imidazolidinone as the above aprotic polar solvent, by-products, which are generally produced, are not produced substantially. The above highly branched perfluoroolefin (A) is preferably employed since the selectivity is high when the highly branched perfluoroolefin (a) is to be obtained.

The term "selectively" employed in this specification describing the reaction for obtaining the above highly branched perfluoroolefin (A) selectively means that the intended product is obtained in a high yield. The above term "high yield" means a yield of 60% by weight or higher.

The reaction for obtaining the above highly branched perfluoroolefin (A) selectively may be one where the starting material radical-carrying molecule is remained unreacted, and the amount of the unreacted material is usually 25% by weight or less of the starting material. For the purpose of obtaining the reaction product of the above highly branched perfluoroolefin (A) at a purity as high as possible, the amount of the unreacted material may be reduced, in some cases, by increasing the amount of addition of the trialkylperfluoroalkylsilane.

In the synthesis of the above highly branched perfluoroolefin, the lower and upper limits of the reaction temperature are generally 0° C. and 70° C., respectively, and the upper limit is preferably 30° C., and the reaction may generally be conducted at room temperature without any particular need of heating, thus the method can be employed easily and enables an energy-saving operation.

The super-stable perfluoroalkyl radical represented by the above general formula (11) is obtained by fluorinating the above highly branched perfluoroolefin.

The highly branched perfluoroolefin employed in the production of the above super-stable perfluoroalkyl radical is preferably the highly branched perfluoroolefin (a), highly branched perfluoroolefin (b) or highly branched perfluoroolefin (c) described above, with the highly branched perfluoroolefin (a) being more preferred since the super-stable perfluoroalkyl radical can be synthesized in a high yield. While two or more species may be employed as the above highly branched perfluoroolefins, it is preferable to use one species for the purpose of increasing the purity of the resultant super-stable perfluoroalkyl radical.

The fluorination in the production of the above super-stable perfluoroalkyl radical is preferably conducted using a fluorine gas. The above fluorine gas may be a diluted one or a neat one without dilution. The dilution of the above fluorine gas may be conducted with an inert gas such as nitrogen or argon. The fluorine gas described above is preferably a pure one.

The fluorination in the production of the above super-stable perfluoroalkyl radical can generally be conducted by introducing a diluted fluorine gas or neat pure fluorine gas into the bottom of the reaction vessel, or also by effecting the reaction under pressure with a fluorine gas in the sealed vessel. The pressure of the fluorine gas may be 1 to 100 atoms (absolute pressure), preferably 1 to 10 atoms (absolute pressure).

Such a fluorination results in the addition of a fluorine atom to one of the double bond-forming carbon atoms of the highly branched perfluoroolefin, whereby obtaining a super-stable perfluoroalkyl radical having an unpaired electron on the other carbon atom of said double bond-forming carbon atoms. In this specification, the above fluorination may be referred to as a "direct fluorination".

During the fluorination described above, when it is conducted under the condition of 1 atom (absolute pressure), the reaction temperature is preferably 40° C. or lower, more preferably 30° C. or lower, for the purpose of raising the yield of the super-stable perfluoroalkyl radical; preferably −10° C. or higher, more preferably 0° C. or higher, for the purpose of promoting the reaction; and when the yield and the promotion of the reaction are taken into account, the upper limit is preferably 10° C., more preferably 5° C., and the lower limit is preferably −10° C., more preferably −5° C.

During the fluorination described above, when it is conducted under the condition of 1 atom (absolute pressure), the aeration time period is generally preferably 500 hours or longer, more preferably 720 hours or longer, for the purpose of raising the yield of the super-stable perfluoroalkyl radical.

The fluorination described above is conducted preferably under pressure and/or at a low temperature such as −5 to 5° C., for instance, for the purpose of reducing the reaction time, preferably under pressure and at a low temperature such as −5 to 5° C. especially for the purpose of industrial application.

The above super-stable perfluoroalkyl radical is not particularly limited provided that it is represented by the above general formula (11).

While Rf as Y and/or Z in the above general formula (11) is not particularly limited provided that it is a low-molecular-pre-radical group having 1 to 16 carbon atoms and may be straight or branched, it is preferably a low-molecular-pre-radical group having 1 to 3 carbon atoms since it is easily purified and analyzed, with a trifluoromethyl group being more preferred. The above Rf is derived from Rf as Y and/or Z in the above general formula (10) representing the above highly branched perfluoroolefin.

As the above super-stable perfluoroalkyl radical, the above super-stable perfluoroalkyl radical (AR) is obtained as a main product from the above highly branched perfluoroolefin (A), the above super-stable perfluoroalkyl radical (BR) is obtained as a main product from the above highly branched perfluoroolefin (B), and the above super-stable perfluoroalkyl radical (CR) is obtained as a main product from the above highly branched perfluoroolefin (C), depending on the species of the highly branched perfluoroolefin employed and the reaction conditions.

Accordingly, as shown in the following scheme, as the main product of the reaction, the above super-stable perfluoroalkyl radical (aR) is obtained from the above highly branched perfluoroolefin (a), the above super-stable perfluoroalkyl radical (bR) is obtained from the above highly branched perfluoroolefin (b) and the above super-stable perfluoroalkyl radical (cR) is obtained from the above highly branched perfluoroolefin (c).

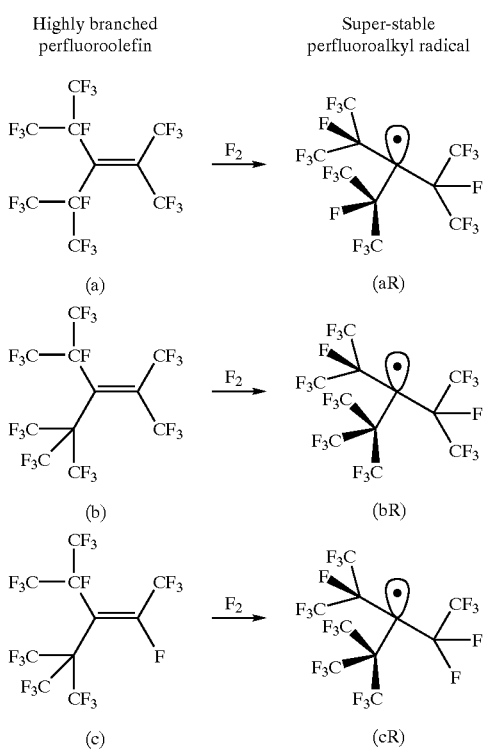

Highly branched perfluoroolefin → Super-stable perfluoroalkyl radical (a) → (aR)
(b) → (bR)
(c) → (cR)

However, the present invention is characterized that the super-stable perfluoroalkyl radical (AR) can be produced by fluorinating the highly branched perfluoroolefin (B)

The method for providing the low-molecular radical of the invention comprises producing the super-stable perfluoroalkyl radical (AR) by fluorinating the highly branched perfluoroolefin (B).

The above highly branched perfluoroolefin (B) and the above super-stable perfluoroalkyl radical (AR) are those described above, and the fluorination mentioned above is conducted by the method similar to the fluorination as described above with regard to the production of the super-stable perfluoroalkyl radical.

The above highly branched perfluoroolefin (B) is fluorinated to produce the above super-stable perfluoroalkyl radical (AR) having a number of carbon atom lower than that of the above highly branched perfluoroolefin (B). In this specification, among the method for providing the low-molecular radical of the invention, the above method comprising fluorinating the highly branched perfluoroolefin (B) to produce the super-stable perfluoroalkyl radical (AR) is sometimes referred to as "the production method of the reduced-carbon super-stable perfluoroalkyl radical", hereinafter.

While the reaction temperature of the production method of the reduced-carbon super-stable perfluoroalkyl radical is not particularly limited, the preferable lower limit and upper limit are −78° C. and 45° C., more preferably −10° C. and 15° C., respectively.

The mechanism of this reaction has not been elucidated clearly, but it is considered such that, by the above fluorination, a fluorine atom is added to a double bond to form an unpaired electron and then the unpaired electron dissociates a single Rf in the general formula (13) representing the above highly branched perfluoroolefin (B) to release as a free radical. This reaction tends to occur easily especially when the fluorination is carried out using a pure fluorine gas at a reaction temperature of 0° C. to room temperature. The above Rf is preferably a trifluoromethyl group.

The above super-stable perfluoroalkyl radical (AR), as described above, can be obtained from the highly branched perfluoroolefin (A) whose number of carbon atom is the same as that of the above super-stable perfluoroalkyl radical (AR) This reaction is proceeded quantitatively when performing the fluorination using a pure fluorine gas at a reaction temperature especially about 0° C.

Therefore, by adjusting the reaction temperature, the intended super-stable perfluoroalkyl radical can be obtained. Such an adjustment of the reaction temperature is considered to be useful especially when the highly branched perfluoroolefin employed is a mixture comprising the above highly branched perfluoroolefin (A) and the above highly branched perfluoroolefin (B).

As the example of the reaction for obtaining the above super-stable perfluoroalkyl radical (AR) by the production method of the reduced-carbon super-stable perfluoroalkyl radical and the reaction for obtaining the same by the production method of the super-stable perfluoroalkyl radical, reactions for obtaining the super-stable perfluoroalkyl radical (aR) from a highly branched perfluoroolefin (b) and from a highly branched perfluoroolefin (a) are described in the following scheme.

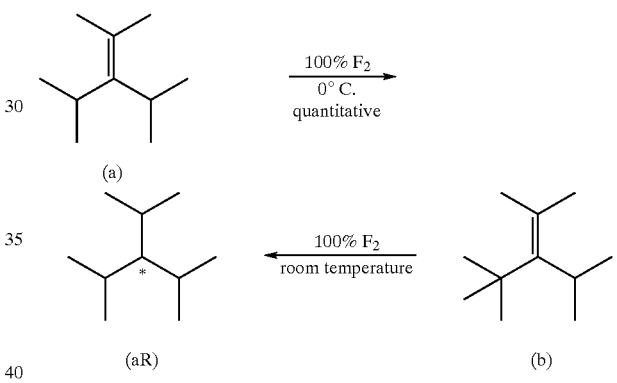

Since the method for providing the low-molecular radical of the invention has the aspects discussed above, it allows a series of reactions to be carried out repetitively as desired, whereby it can be applied industrially. The method for providing the low-molecular radical of the invention, when utilizing a super-stable perfluoroalkyl-based radical (α-β.) comprising a low-molecular radical (α.) and a carrying molecule thereof (β) industrially as a recyclable radical-generating system, allows these chemical species (α.), (β) and (α-β.) to fulfill all of the following 5 requirements:

Requirement (1): The low-molecular radical (α.) can easily be released from (α-β.) by heating where necessary;
Requirement (2): (α-β.) has an extremely high chemical stability and undergoes absolutely no change over a period of the order of years at room temperature;
Requirement (3): (β) is regenerated simultaneously with the thermal release of the low-molecular radical (α.);
Requirement (4): Regenerated (β) can easily be recovered; and,
Requirement (5): (α-β.) can easily be synthesized using the regenerated (β);
whereby providing a recyclable radical-generating system.

The method for providing the low-molecular radical of the invention can be utilized in the radical-carrying molecule which maintains the low-molecular radical chemically at the level of molecule and releases the same when necessary, and in the recycling technology which regenerates and utilizes the above radical-carrying molecule. The above radical-carrying molecule is a recyclable molecule which enables this recycling technology. According to the method for providing the low-molecular radical of the invention, the super-stable perfluoroalkyl-based radical, especially the super-stable perfluoroalkyl radical (aR) can be utilized efficiently.

According to the method for providing the low-molecular radical of the invention, the above radical-carrying molecule is generated as a result of the radical releasing reaction, and from this radical-carrying molecule, the super-stable perfluoroalkyl-based radical is easily generated as a result of the super-stable radical generating reaction, whereby enabling a continuous supply of the low-molecular radical.

Since the method for providing the low-molecular radical of the invention is one releases only the low-molecular radical, which is industrially highly applicable, out of the reaction system of the above method for providing the low-molecular radical and utilizes a molecule formed upon release of the low-molecular radical as a radical-carrying molecule repetitively in a shuttle-like manner, the method can provide a radical source which is advantageous in view of so-called atom economy, cost efficiency and environmental protection.

The radical-carrying molecule which is used in the above method for providing the low-molecular radical is also encompassed by the invention.

The above radical-carrying molecule is defined as discussed above, and is preferably the trimer B.

Since the above super-stable perfluoroalkyl-based radical is extremely and sufficiently stable, a low-molecular radical such as trifluoromethyl released upon heating at, for example, 90° C. or higher can be employed not only as a polymerization initiator in a polymer synthesis, but also as a standard substance for electron spin resonance (ESR), surface treatment reagent, leak checking reagent for a container with a complicated shape, emulsion as a contrast agent for biological imaging.

Among them, the above super-stable perfluoroalkyl radical (aR) and the above super-stable perfluoroalkyl radical (bR), especially the above super-stable perfluoroalkyl radical (aR), can be employed preferably as standard substrates for ESR, since they are highly symmetric.

A process for polymerization of the invention comprises using the low-molecular radical released by the method for providing the low-molecular radical described above as a polymerization initiator.

In the process for polymerization of the invention, the temperature at least of the radical releasing reaction system should be 80° C. or higher for the purpose of releasing the above low-molecular radical, no particular heating means is required since the polymerization is usually accompanied with the generation of polymerization heat, whereby allowing both of the polymerization reaction and the radical releasing reaction to be carried out in a thermally efficient manner.

In the process for polymerization of the invention, the dimerization reaction of the super-stable perfluoroalkyl-based radicals and the binding of the super-stable perfluoroalkyl-based radical with the propagating polymer chain terminal are difficult to occur due to the steric hindrance of the super-stable perfluoroalkyl-based radical. Accordingly, the method can be practiced without separating the reaction system of the above process for polymerization from the reaction system of the method for providing the low-molecular radical.

A polymer which is obtained by the above process for polymerization is also encompassed by the invention.

In the method for providing the low-molecular radical of the invention, which is constituted as described above, an olefin produced upon the release of the above low-molecular radical is used as the radical-carrying molecule to synthesize the low-molecular-radical-generating substance, whereby a series of the reactions can be repeated and the low-molecular radical can be provided continuously.

EXAMPLE

The following examples illustrate the present invention in further detail. These examples are, however, by no means limitative of the scope of the present invention. For gas chromatography measurement, a capillary column (NB-1, 0.25 μm, 1.5 mm ID×60 m) was used and an FID was used as a detector. For preparative gas chromatography, a packed column whose mobile phase was Fomblin was used. Mass spectroscopy (MS) was measured using a gas chromatograph-quadrupole mass spectrometer (GC-MS), with the ionization voltage of 70 eV.

Paramagnetic nuclear magnetic resonance absorption spectrum (ESR) was measured using FC-72 (perfluorocarbon containing perfluorohexane as a main component) as a solvent.

Example 1
System for Generating Recyclable Trifluoromethyl Radical in Trifluoromethylation Reaction of Benzene A 500-mL round bottom flask is charged with 100 ml of benzene and perfluoro(2,4-dimethyl-3-isopropyl-3-pentyl) (10 mmol, 5.19 g), and fitted with a fluororesin-coated magnetic stirrer and Dimroth funnel condenser. The reactants were stirred thoroughly with heating under reflux in an oil bath. After refluxing for 12 hours, upon cooling on an ice-water bath, perfluoro(4-methyl-3-isopropyl-2-pentene) was precipitated as a fluoro-layer and formed a colorless and transparent lower layer, which was separated using a glass Pasteur pipette (4.45 g, recovery rate: 99%). The benzene layer was analyzed by a capillary gas chromatography (assayed using benzotrifluoride reference standard), which was revealed to contain benzotrifluoride at 77% yield.

Perfluoro(4-methyl-3-isopropyl-2-pentene) thus recovered was added with trifluoromethyltrimethylsilane (2.84 g, 20 mmol), 1,3-dimethyl-2-imidazolidinone (10 ml) and acidic potassium fluoride (78 mg, 1 mmol), and the mixture was stirred vigorously at room temperature for 1 hour. The yield of the product perfluoro(2,4-dimethyl-3-isopropyl-2-pentene) forming a lower fluoro-layer was 92% (455 mg). The recovery rate of the raw material perfluoro(4-methyl-3-isopropyl-2-pentene) was 8%.

Perfluoro(2,4-dimethyl-3-isopropyl-2-pentene) thus obtained was fluorinated directly using a pure fluorine for 30 days at 0° C. to obtain perfluoro(2,4-dimethyl-3-isopropyl-3-pentyl) (460 mg) quantitatively. This Example revealed that a radical generating system was provided in which perfluoro(4-methyl-3-isopropyl-3-pentene) and perfluoro(2,4-dimethyl-3-isopropyl-3-pentyl) were recyclable in the trifluoromethylation reaction of benzene.

What is claimed is:

1. A method for providing a low-molecular radical which comprises a super-stable radical generating reaction for generating a super-stable perfluoroalkyl-based radical from a radical-carrying molecule and a radical releasing reaction for releasing the low-molecular radical from said super-stable perfluoroalkyl-based radical, said radical-carrying molecule being generated as a result of said radical releasing reaction.

2. The method for providing the low-molecular radical according to claim 1,
wherein the super-stable radical generating reaction comprises introducing a low-molecular-pre-radical group into the radical-carrying molecule,
said low-molecular-pre-radical group being a group having the same structure as the low-molecular radical.

3. The method for providing the low-molecular radical according to claim 1,
wherein the radical-carrying molecule is a hexafluoropropene trimer.

4. The method for providing the low-molecular radical according to claim 1,
wherein the low-molecular radical is a straight or branched perfluoroalkyl having 1 to 16 carbon atoms or a free radical represented by the following general formula (1):

$$RfRa^h \qquad (1)$$

in the formula, $Ra^h$ represents a nitrogen atom having two unpaired electrons, an oxygen atom having one unpaired electron or a sulfur atom having one unpaired electron, and Rf represents a straight or branched perfluoroalkyl group having 1 to 16 carbon atoms.

5. The method for providing the low-molecular radical according to claim 1,
wherein the low-molecular radical is a linear substituted aminyl represented by the following general formula (2):

$$Rf_2Ra^N \qquad (2)$$

in the formula, $Ra^N$ represents a nitrogen atom having one unpaired electron and each Rf is the same or different from each other and represents a straight or branched perfluoroalkyl group having 1 to 16 carbon atoms,
or a cyclic substituted aminyl represented by the following general formula (3):

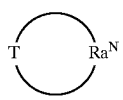 (3)

in the formula, $Ra^N$ is defined as described above, T represents a perfluoroalkylene group having 4 to 6 carbon atoms and having or not having 1 to 2 ethereal oxygen.

6. The method for providing the low-molecular radical according to claim 1,
wherein the super-stable perfluoroalkyl-based radical is a free radical represented by the following general formula (4):

$$[(CF_3)_2CF][(CF_3)_2CY']Ra^c\text{---}CF(CF_3)Z' \qquad (4)$$

in the formula, $Ra^c$ represents a carbon atom having one unpaired electron, and Y' and Z' are the same or different and each represents F or the low-molecular-pre-radical group, provided that Y' and Z' are not simultaneously F.

7. The method for providing the low-molecular radical according to claim 6,
wherein the super-stable perfluoroalkyl-based radical is a super-stable perfluoroalkyl-based radical (AR') represented by the following general formula (5):

$$[(CF_3)_2CF]_2Ra^c\text{---}CF(CF_3)Z' \qquad (5)$$

in the formula, $Ra^c$ represents a carbon atom having one unpaired electron, and Z' represents the low-molecular-pre-radical group.

8. The method for providing the low-molecular radical according to claim 2,
wherein the low-molecular-pre-radical group is a straight or branched perfluoroalkyl group having 1 to 16 carbon atoms or a group represented by the following general formula (6):

$$RfQ\text{-} \qquad (6)$$

in the formula, Q represents a nitrogen atom, an oxygen atom or a sulfur atom, and Rf represents a straight or branched perfluoroalkyl group having 1 to 16 carbon atoms.

9. The method for providing the low-molecular radical according to claim 2,
wherein the low-molecular-pre-radical group is a linear substituted aminyl group represented by the following general formula (7):

$$Rf_2N\text{---} \qquad (7)$$

in the formula, each Rf is the same or different from each other and represents a straight or branched perfluoroalkyl group having 1 to 16 carbon atoms,
or a cyclic substituted aminyl group represented by the following general formula (8):

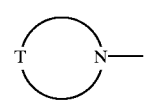 (8)

in the formula, T represents a perfluoroalkylene group having 4 to 6 carbon atoms and having or not having 1 to 2 ethereal oxygen.

10. The method for providing the low-molecular radical according to claim 1,
wherein the radical releasing reaction is one carried out by means of heat and/or light.

11. The method for providing the low-molecular radical according to claim 2,
wherein the introduction of the low-molecular-pre-radical group into the radical-carrying molecule comprises using a hexafluoropropene trimer as said radical-carrying molecule and reacting said hexafluoropropene trimer with a trialkylperfluoroalkylsilane represented by the following general formula (9):

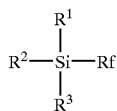   (9)

in the formula, Rf represents a straight or branched perfluoroalkyl group having 1 to 16 carbon atoms, and $R^1$, $R^2$ and $R^3$ are the same or different and each represents an alkyl group caving 1 to 3 carbon atoms, in an aprotic polar solvent using a fluoride ion as a catalyst to thereby form a highly branched perfluoroolefin represented by the following general formula (10):

$$[(CF_3)_2CF][(CF_3)_2CY]C\!\!=\!\!C(CF_3)Z \tag{10}$$

in the formula, Y and Z are the same or different and each represents F or Rf, provided that Y and Z are not simultaneously F, and Rf is defined as described above.

12. The method for providing the low-molecular radical according to claim 11, wherein the super-stable radical generating reaction further comprises fluorinating the highly branched perfluoroolefin to thereby form a super-stable perfluoroalkyl radical represented by the following general formula (11):

$$[(CF_3)_2CF][(CF_3)_2CY]Ra^c\!\!-\!\!CF(CF_3)Z \tag{11}$$

in the formula, $Ra^c$ represents a carbon atom having one unpaired electron, Y and Z are the same or different and each represents F or Rf, provided that Y and Z are not simultaneously F, and Rf represents a straight or branched perfluoroalkyl group having 1 to 16 carbon atoms.

13. The method for providing the low-molecular radical according to claim 11, wherein the highly branched perfluoroolefin is perfluoro(2,4-dimethyl-3-isopropyl-2-pentene), perfluoro(2,4,4-trimethyl-3-isopropyl-2-pentene) or perfluoro(4,4-dimethyl-3-isopropyl-2-pentene).

14. The method for providing the low-molecular radical according to claim 11, wherein the aprotic polar solvent is 1,3-dimethyl-2-imidazolidinone, and wherein the highly branched perfluoroolefin is a highly branched perfluoroolefin (A) represented by the following general formula (12):

$$[(CF_3)_2CF]_2C\!\!=\!\!C(CF_3)Rf \tag{12}$$

in the formula, Rf represents a straight or branched perfluoroalkyl group having 1 to 16 carbon atoms, said highly branched perfluoroolefin (A) being formed selectively.

15. The method for providing the low-molecular radical according to claim 14, wherein the highly branched perfluoroolefin (A) is perfluoro(2,4-dimethyl-3-isopropyl-2-pentene).

16. The method for providing the low-molecular radical according to claim 12, wherein the highly branched perfluoroolefin is a highly branched perfluoroolefin (B) represented by the following general formula (13):

$$[(CF_3)_2CF][(CF_3)_2CRf]C\!\!=\!\!C(CF_3)Rf \tag{13}$$

in the formula, each Rf is the same or different from each other and represents a straight or branched perfluoroalkyl group having 1 to 16 carbon atoms, and wherein the super-stable perfluoroalkyl radical is a super-stable perfluoroalkyl radical (AR) represented by the following general formula (11a):

$$[(CF_3)_2CF]_2Ra^c\!\!-\!\!CF(CF_3)Rf \tag{11a}$$

in the formula, $Ra^c$ represents a carbon atom having one unpaired electron and Rf is defined as described above.

17. The method for providing the low-molecular radical according to claim 16, wherein the highly branched perfluoroolefin (B) is perfluoro(2-4-4-trimethyl-3-isopropyl-2-pentene).

18. The method for providing the low-molecular radical according to claim 11, wherein the trialkylperfluoroalkylsilane is trifluoromethyltrimethylsilane.

19. The method for providing the low-molecular radical according to claim 3, wherein the radical-carrying molecule is perfluoro(4-methyl-3-isopropyl-2-pentene).

20. The method for providing the low-molecular radical according to claim 4, wherein the low-molecular radical is trifluoromethyl.

21. The method for providing the low-molecular radical according to claim 7, wherein the super-stable perfluoroalkyl-based radical is perfluoro(2,4-dimethyl-3-isopropyl-3-pentyl).

22. A radical-carrying molecule which is used in the method for providing the low-molecular radical according to claim 1.

23. The radical-carrying molecule according to claim 22 which is perfluoro(4-methyl-3-isopropyl-2-pentene).

24. A process for polymerization which comprises using the low-molecular radical released by the method for providing the low-molecular radical according to claim 1 as a polymerization initiator.

25. A polymer which is obtained by the production method of the polymer according to claim 24.

* * * * *

UNITED STATES PATENT AND TRADEMARK OFFICE
CERTIFICATE OF CORRECTION

PATENT NO. : 6,818,800 B2
DATED : November 16, 2004
INVENTOR(S) : Taizo Ono et al.

It is certified that error appears in the above-identified patent and that said Letters Patent is hereby corrected as shown below:

Column 18,
Line 28, please delete "perfluoro(2-4-4-trimethyl-3-isopropyl-2-pentene) and insert -- perfluoro(2,4,4-trimethyl-3-isopropyl-2-pentene) --

Signed and Sealed this

Seventeenth Day of May, 2005

JON W. DUDAS
*Director of the United States Patent and Trademark Office*